United States Patent [19]

Barlet

[11] Patent Number: 5,070,083

[45] Date of Patent: Dec. 3, 1991

[54] FUNGICIDAL ALUMINUM TRIS-ALKYL-PHOSPHONATE COMPOSITION

[75] Inventor: Denis Barlet, Lyons, France

[73] Assignee: Rhone Poulenc Agrochimie, S.A., Lyons, France

[21] Appl. No.: 469,302

[22] Filed: Jan. 24, 1990

Related U.S. Application Data

[60] Division of Ser. No. 891,547, Jul. 29, 1986, Pat. No. 4,935,410, which is a continuation-in-part of Ser. No. 770,653, Aug. 29, 1985, abandoned, which is a continuation-in-part of Ser. No. 870,983, Jun. 5, 1986, abandoned, which is a continuation of Ser. No. 684,987, Dec. 21, 1984, abandoned, which is a continuation of Ser. No. 595,460, Mar. 30, 1984, abandoned.

[30] Foreign Application Priority Data

Mar. 31, 1983 [FR] France ................ 83 05562
Aug. 29, 1984 [FR] France ................ 84 13557

[51] Int. Cl.$^5$ ............ A01N 57/10; A01N 57/00; A61K 31/66; C07F 9/02
[52] U.S. Cl. ............................ 514/144; 514/75; 514/76; 558/71
[58] Field of Search ............ 514/144, 75, 76, 134, 514/135, 494; 558/71

[56] References Cited

U.S. PATENT DOCUMENTS

| | | | |
|---|---|---|---|
| 4,075,324 | 2/1978 | Thizy et al. | 424/128 |
| 4,075,327 | 2/1978 | Jorgensen et al. | 424/273 R |
| 4,139,616 | 2/1979 | Ducret et al. | 424/222 |
| 4,335,109 | 6/1982 | Hill | 424/140 |
| 4,366,150 | 12/1982 | Yamada et al. | 424/199 |

FOREIGN PATENT DOCUMENTS 064283 11/1982 European Pat. Off.
2137498 10/1984 United Kingdom.

OTHER PUBLICATIONS

Gregory, Thomas C.—Uses and Applications of Chemical and Related Material, p. 133.

*Primary Examiner*—Frederick E. Waddell
*Assistant Examiner*—T. J. Criares
*Attorney, Agent, or Firm*—Morgan & Finnegan

[57] ABSTRACT

This present invention relates to fungicidal compositions comprising an aqueous solution of an aluminum salt of alkyl phosphates strabilized with the salt of a weak acid and a strong base. The stabilized aqueous solution can be used to prevent or treat fungal diseases in plants by spraying, soaking the roots or injecting into the trunks of shrubs or trees.

7 Claims, No Drawings

FUNGICIDAL ALUMINUM TRIS-ALKYL-PHOSPHONATE COMPOSITION

This is a divisional of co-pending application Ser. No. 06/891,547 filed July 29, 1986, now U.S. Pat. No. 4,935,410, which is a continuation-in-part of U.S. application Ser. No. 06/770,653 filed Aug. 29, 1985, abandoned and also is a continuation-in-part of earlier U.S. application Ser. No. 06/870,983 filed June 5, 1986, abandoned, which is a continuation of U.S. application Ser. No. 06/684,987 filed Dec. 21, 1984, abandoned, which is a continuation of U.S. application Ser. No. 06/595,460 filed Mar. 30, 1984, abandoned. The foregoing applications are hereby incorporated by reference.

BACKGROUND OF THE INVENTION

The present invention relates to new fungicidal compositions comprising a stabilized aqueous solution of the salt of a phosphorous acid ester as an active ingredient, and methods of treating fungal diseases in plants with these compositions.

Subject matter relating to this application is described in French Patent 2,254,276, which corresponds to U.S. Pat. No. 4,139,616, and is hereby incorporated by reference. French Patent 2,254,276 describes the use of compositions containing the metal salt of an alkyl ester of phosphorous acid, in particular, aluminum tris-ethyl-phosphonate, to combat fungal diseases in plants. The compositions of French Patent 2,254,276 contain, as the active ingredient, at least one salt of an alkyl-phosphorous acid corresponding to the general formula:

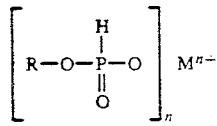

in which R is an optionally halogenated or nitrated, linear or branched alkyl radical containing from 1 to 18 carbon atoms and preferably from 1 to 8 carbon atoms, an optionally halogenated alkenyl or alkinyl radical, an alkoxy alkyl radical, an alkenoxy alkyl radical, the hydrocarbon portion of these four types of radicals containing from 1 to 8 and preferably from 1 to 5 carbon atoms, a cyclohexyl radical, an optionally substituted aryl radical, preferably phenyl, or aryl alkyl radical, preferably phenyl alkyl, or a heterocyclic radical optionally attached to the oxygen through an aliphatic chain, preferably tetrahydrofurfuryl, M represents a hydrogen atom, ammonium cation, ammonium substituted by 1 to 4 alkyl or hydroxy alkyl radicals containing from 1 to 5 carbon atoms or 1 to 2 cyclohexyl radicals of a phenyl radical, or a cation of a metal from the group comprising the alkali metals, preferably sodium and potassium, alkaline earth metals, preferably magnesium, barium, calcium, and polyvalent metals such as, preferably, zinc, manganese, copper (I) and (II), iron, nickel, aluminum, and n is an integer equal to the valency of M.

These compositions have been found to be effective against many phytophagous fungi, such as Phycomycetes, particularly Plasmopara viticola and various Phytophthora. In practice, aluminum tris-ethyl-phosphonate or aluminum ethyl phosphite known commercially as Phosethyl Al, is applied to a plant in the form of a suspension of a wettable powder by spraying the leaves. Although the treatment is quite effective for protecting vines against fungal attack, the effectiveness of this treatment against fungal diseases in tropical plants has been less than desirable. It has been found that it takes too long a time to cure a plant which has been attacked, often heavily, by fungi of the Phytophthora type, such as Phytophthora cinnamomi which causes the rotting of avocado and citrus fruit trees.

The reason that the spray treatment has not been very effective is because the amount of active ingredient absorbed via the leaves of a plant is relatively small. This small amount is insufficient if the plant has already been attacked by fungi and has to be cured. This necessitates more spraying, making the treatment prohibitively expensive and very slow. At times, if the plant has been severely attacked by fungi even multiple treatments are inadequate.

Moreover, Phosethyl Al undergoes rapid hydrolysis in an aqueous medium, and over a period of time there is a substantial and progressive decrease in the amount of active ingredient in the solution. It is thus impossible to have concentrated aqueous compositions which are stable over a period of time

SUMMARY OF THE INVENTION

The present invention relates to a stabilized fungicidal composition comprised of an aqueous solution of Phosethyl Al and the water-soluble salt of a weak acid and a strong base. Secondly, the present invention relates to a process for stabilizing aqueous solutions of Phosethyl Al, by adding a stabilizer, a water-soluble salt of a weak acid and a strong base, to the aqueous Phosethyl Al solution. The stabilized solution can be used to prevent or treat fungal diseases in plants by spraying. The present invention further relates to an effective method of treating fungal diseases in shrubs or trees by injecting a stabilized aqueous solution of Phosethyl Al into the trunks of the shrubs or trees.

DETAILED DESCRIPTION OF THE INVENTION

According to the present invention, aqueous solutions of Phosethyl Al can be stabilized by the addition of a water soluble salt of a weak acid and a strong base.

Weak acids according to the present invention are to be understood as comprising weak mineral acids, such as: phosphorous acid or phosphonic acid; organic aliphatic acids, such as acetic acid, propionic acid, butyric acid, fumaric acid, oxalic acid, lactic acid or citric acid; or amino acids, such as ethylenediaminetetraacetic acid. Preferred weak acids are organic aliphatic acids and amino acids.

Strong bases which may be used are organic bases, such as tertiary amines, or, preferably, mineral bases, such as alkali metal and alkaline earth metal hydroxides, or zinc hydroxide, and most preferably hydroxides with good solubility in water, such as sodium hydroxide, potassium hydroxide, lime or zinc hydroxide.

The zinc metal ion in the resulting zinc salt stabilizers has a valence of (+2). The amount of stabilizer depends on the nature the stabilizer and the concentration of Phosethyl Al in the aqueous composition. In fact, if the amount of stabilizer present is too small or too large, the solution will not remain clear, indicating insufficient solubililzation of the active ingredient, thereby limiting the effectiveness of the composition. Surprisingly, it has been found that the appropriate amount of stabilizer does not correspond to a stoichiometric amount, i.e. an amount that is the mole equivalent of the stabilizer per mole of Phosethyl Al. Generally, amounts from 30 to 80% of the stoichiometric amount of Phosethyl Al are suitable. For example, in the cases of zinc acetate and calcium acetate, use of about half of the stoichiometric amount results in a stable clear solution, while twice this amount gives rise to a precipitate.

The aqueous composition according to the invention may also contain other water-soluble adjuvants, such as surface-active agents. It may also contain certain oligoelements, such as salts of zinc, manganese, iron or boron in suitable amounts to promote the growth of the trees or combat mineral deficiencies.

According to the invention, Phosethyl Al may be present in the compositions in a concentration of about 1 g to 120 g/liter, preferably 10 g to 120 g/litter, and most preferably 100 g to 120 g/liter.

This solution can be applied by any suitable method, such as spraying of the leaves, or soaking of the roots. Excellent results have been obtained by injecting the composition according to the present invention into the trunks of diseased trees, such as, e.g., avocado, citrus fruit, hevea or cocoa trees.

The treatment is carried out by first making holes around the trunk of the tree, then injecting into the holes with an appropriate device an amount of the stabilized aqueous Phosethyl Al composition, in the range of from 0.1 g to 5 g/m$^2$ of soil covered by the foliage. The injection may be made with or without applying pressure. However, since the liquid is absorbed slowly, it is preferable to apply pressure while injecting. When all of the solution has been injected, it may be desirable to block the hole or holes with the aid of a material, such as a wax, which is non-aggressive towards plant tissues. The wax may contain adjuvants, such as disinfectants to reduce the risk of introducing other diseases The treatment needs to be repeated only a few times. This is in contrast to the numerous spray treatments which may be necessary. For example, on a severely attacked tree effective treatment can be obtained in the first year with two injections followed by a further treatment in the following year to completely cure the tree of the fungal disease. If desired, treatment may be applied once per year thereafter to keep the tree healthy. The effectiveness of the treatment is remarkable as evidenced by the fact that heavily attacked trees have been cured within two years. This result is particularly surprising since other systemic fungicides, which are usually active on these fungi, are ineffective when injected under similar conditions.

The following examples illustrate the preparation of a composition according to the invention and its application by injection into trunks of diseased trees.

EXAMPLE 1

The following compositions were prepared using the amount shown by weight in grams:

|  | Control | Solutions 1 | 2 |
| --- | --- | --- | --- |
| Technical grade 98% pure Phosethyl Al | 102 | 102 | 102 |
| Calcium acetate | — | 33 | 67 |
| Water gsp 1 liter | 898 | 865 | 831 |

EXAMPLE 2

The following compositions were prepared using the amount shown by weight in grams. In the following compositions, dihydrated zinc acetate defines the salt as having two rather than three water molecules:

|  | Control | Solutions 3 | 4 |
| --- | --- | --- | --- |
| Technical grade 98% pure Phosethyl Al | 102 | 102 | 102 |
| Zinc acetate dihydrated | — | 47 | 70 |
| Water gsp 1 liter | 948 | 916 | 898 |

In Example 1, the amounts of calcium acetate added correspond to one half the stoichiometric amount for Solution 1 and to a single stoichiometric amount for Solution 2. The stoichiometric amount is the mole equivalents of the stabilizer per mole of Phosethyl Al. In Example 2, the amounts of zinc acetate added correspond to one half and three quarters of the stoichiometric amount of Phosethyl Al for Solutions 3 and 4, respectively. The addition of these stabilizing amounts of calcium acetate to Solutions 1 and 2 of Example 1 and zinc acetate to Solutions 3 and 4 of Example 2 is sufficient so as to reduce the relative degradation of Phosethyl Al from 100% to a percentage indicating an acceptably stabilized solution.

Solutions 1 and 2 and the control solution of Example 1 and Solutions 3 and 4 and the control solution of Example 2 were subjected to stability testing at 50° C. for 1 month, after which the relative degradation of Phosethyl Al and the appearance of the solutions were measured and evaluated. The degree of degradation of Phosethyl Al is measured by reacting Phosethyl Al with diazomethane thereby obtaining a methyl phosphonate or ethyl phosphonate which is then measured by gas-liquid chromatography.

The results for the solutions of Example 1 are shown in Table A:

TABLE A

| Evaluation criterion after 1 month at 50° C. | Control | Solutions 1 | 2 |
| --- | --- | --- | --- |
| Relative degradation of Phosethyl Al | 100% | 12% | 12% |
| Appearance of the solution (initially clear) | precipitate | clear | slight precipitate |

With respect to the solutions of Example 2, the results are shown in Table B:

TABLE B

| Evaluation criterion after 1 month at 50° C. | Control | Solutions 3 | 4 |
| --- | --- | --- | --- |
| Relative degradation of Phosethyl Al | 100% | 13% | 16% |
| Appearance of the solution (initially clear) | precipitate | clear | clear |

As Table A illustrates, the Phosethyl Al, after 1 month at 50° C., has undergone complete degradation in the control solution as evidenced by the formation of a precipitate. Prepared according to the invention, Solution 1, a clear solution, is completely stabilized. In Solution 2, prepared according to the invention, the degradation of Phosethyl Al has been limited in an acceptable manner as evidenced by the formation of only a slight precipitate. Solution 1 has been found to be effective in treating diseased avocado trees when it is injected into the trunks of the diseased trees.

Table B similarly demonstrates that after 1 month at 50° C., the Phosethyl Al has undergone complete degradation in the control solution as evidenced by the formation of a precipitate. In Solutions 3 and 4, prepared according to the invention, the degradation of Phosethyl Al has been limited in an acceptable manner. Solution 3, an absolutely clear solution, is completely effective. Solution 4, a nearly clear solution, while not as effective and Solution 3, is sufficiently stable to remain effective.

EXAMPLE 3

Two compositions are prepared by diluting Solution 1, in Example 1, once and, respectively, twice. Compositions containing, respectively, 51 and 20.5 grams of 98% pure Phosethyl Al and 16.5 and 8.25 grams of calcium acetate are thus obtained.

EXAMPLE 4

Two compositions are prepared by diluting Solution 2, in Example 2, once and, respectively, twice. Compositions containing, respectively, 51 and 25.5 grams of 98% pure Phosethyl Al and 23.5 and 11.75 grams of zinc acetate per liter are thus obtained.

What is claimed is:

1. A stabilized fungicidal composition against phytophagous and phytophthora fungal infection in plants consisting of an aqueous solution of:
   (a) about 1 g to 120 g per liter of solution of aluminum tris-ethyl-phosphonate; and
   (b) 0.3 to 0.8 of the stoichiometric amount per mole of aluminum tris-ethyl-phosphonate, of a stabilized salt selected from the group consisting of calcium acetate and zinc acetate.

2. A stabilized fungicidal composition according to claim 1, wherein the stabilizer salt is calcium acetate.

3. A stabilized fungicidal composition according to claim 1, wherein the stabilizer salt is zinc acetate.

4. A stabilized fungicidal composition according to claim 1, wherein the concentration of aluminum tris-ethyl-phosphonate in the solution is about 10 to 110 g/liter.

5. A stabilized fungicidal composition according to claim 1, wherein the stabilizer salt is about 0.5 of the stoichiometric amount.

6. A stabilized fungicidal composition according to claim 1, wherein the concentration of the aluminum tris-ethyl-phosphonate is in the range of about 100 g to 120 g/liter, the stabilizer salt is calcium acetate and is about 0.5 of the stoichiometric amount.

7. A stabilized composition according to claim 1, wherein the concentration of aluminum tris-ethyl-phosphonate is in the range of about 100 g to 120 g/liter, the stabilizer salt is zinc acetate and is about 0.5 of the stoichiometric amount.

* * * * *